US010377836B2

(12) United States Patent
Joung et al.

(10) Patent No.: US 10,377,836 B2
(45) Date of Patent: Aug. 13, 2019

(54) GROUP 4 TRANSITION METAL COMPOUND AND USE THEREOF

(71) Applicant: HANWHA CHEMICAL CORPORATION, Seoul (KR)

(72) Inventors: Ui Gab Joung, Daejeon (KR); Kil Sagong, Daejeon (KR); Sung Hae Jun, Gyeonggi-do (KR); Dong Ok Kim, Seoul (KR); Hye Ran Park, Gyeongsangbuk-do (KR); In Jun Lee, Gyeonggi-do (KR)

(73) Assignee: HANWHA CHEMICAL CORPORATION, Seoul (KR)

( * ) Notice: Subject to any disclaimer, the term of this patent is extended or adjusted under 35 U.S.C. 154(b) by 56 days.

(21) Appl. No.: 15/536,100

(22) PCT Filed: Dec. 23, 2015

(86) PCT No.: PCT/KR2015/014187
§ 371 (c)(1),
(2) Date: Jun. 14, 2017

(87) PCT Pub. No.: WO2016/105124
PCT Pub. Date: Jun. 30, 2016

(65) Prior Publication Data
US 2017/0369605 A1    Dec. 28, 2017

(30) Foreign Application Priority Data
Dec. 23, 2014 (KR) .......................... 10-2014-0187188

(51) Int. Cl.
*C08F 4/64* (2006.01)
*C08F 4/76* (2006.01)
(Continued)

(52) U.S. Cl.
CPC .................. *C08F 4/64* (2013.01); *C07F 7/00* (2013.01); *C08F 2/06* (2013.01); *C08G 61/02* (2013.01)

(58) Field of Classification Search
CPC .......................... C08F 4/60072; C08F 4/64072
See application file for complete search history.

(56) References Cited

U.S. PATENT DOCUMENTS 9,109,055 B2    8/2015   Kim

FOREIGN PATENT DOCUMENTS

EP         3187499 A1      7/2017
EP         3239156 A1     11/2017
(Continued)

OTHER PUBLICATIONS

Hwang E.Y.; Park, G.H.; Lee, C.S.; Kang, Y.Y.; Lee, J.; Lee, B.Y. Dalton Transactions 2015, 44, 3845-3855 (Year: 2015).*
(Continued)

*Primary Examiner* — Rip A Lee
(74) *Attorney, Agent, or Firm* — Marshall, Gerstein & Borun LLP

(57) ABSTRACT

The present invention relates to a novel Group 4 transition metal compound, a method for preparing the compound, a catalyst composition comprising the compound, and a method for preparing a polyolefin comprising performing a polymerization reaction of olefin monomers, in the presence of the catalyst composition. Since the Group 4 transition metal compound of the present invention exhibits an excellent catalytic activity in polyolefin synthesis reactions, as well as having excellent thermal stability, it can be used for polyolefin synthesis reactions at high temperatures, and by changing the type of a central metal and ligand, the weight average molecular weight of synthesized polyolefins and the octene content in the polymer can be controlled. Therefore, (Continued)

it can be effectively used in polyolefin synthesis processes in which grades are controlled.

20 Claims, 1 Drawing Sheet

(51) Int. Cl.
    *C07F 7/00*    (2006.01)
    *C08F 2/06*    (2006.01)
    *C08G 61/02*   (2006.01)

(56) References Cited

FOREIGN PATENT DOCUMENTS

KR    10-2008-0000355 A    1/2008
KR    10-2014-0018724 A    2/2014

OTHER PUBLICATIONS

International Search Report for International Application No. PCT/KR2015/014187, dated Apr. 1, 2016.
Hwang, Eun Yeong et al., Preparation of octahydro- and tetrahydro-[1,10]phenanthroline zirconium and hafniumcomplexes for olefin polymerization, Dalton Transactions, vol. 44, pp. 3845-3855 (2015).
Chaudhry, S. C. et al., Proceedings of the National Academy of Sciences, India, vol. 75, A, Part 1, pp. 11-15, Mar. 2005.
Malhotra, K. C. et al., Acceptor Properties of Titanium 2-Naphthyloxides, vol. 3, No. 1, pp. 125-128 (1984).
Boussie et al., Journal of the American Chemical Society Articles, 2003, vol. 125: pp. 4306-4317.
Lin et al., Boryl-Metal Bonds Facilitate Cobalt/Nickel-Catalyzed Olefin Hydrogenation, J. American Chemical Society, vol. 136, pp. 13672-13683 (Sep. 2, 2014).
Supplementary European Search Report issued in European Patent Application No. 15873651 dated Aug. 16, 2018.
Tabernero V et al., Early transition metal derivatives stabilised by the phenylenediamido 1,2-C"6H"4(NCH"2tBu)"2 ligand: Sythesis, characterisation and reactiviy studies: Crystal structures of [Ta{1,2-C"6H"4(NCH"2tBu)"2}(NMe"2) (@m-NMe"2)}"2" *Polyhedron, Pergamon Press*, Oxford, vol. 28, No. 13 (Sep. 2009).
Sung Hae Jun et al., "Preparation of Phosphine-Amido Hafnium and Zirconium Complexes for Olefin Polymerization," *Organometallics*, vol. 32, No. 24 (Dec. 2013).

\* cited by examiner

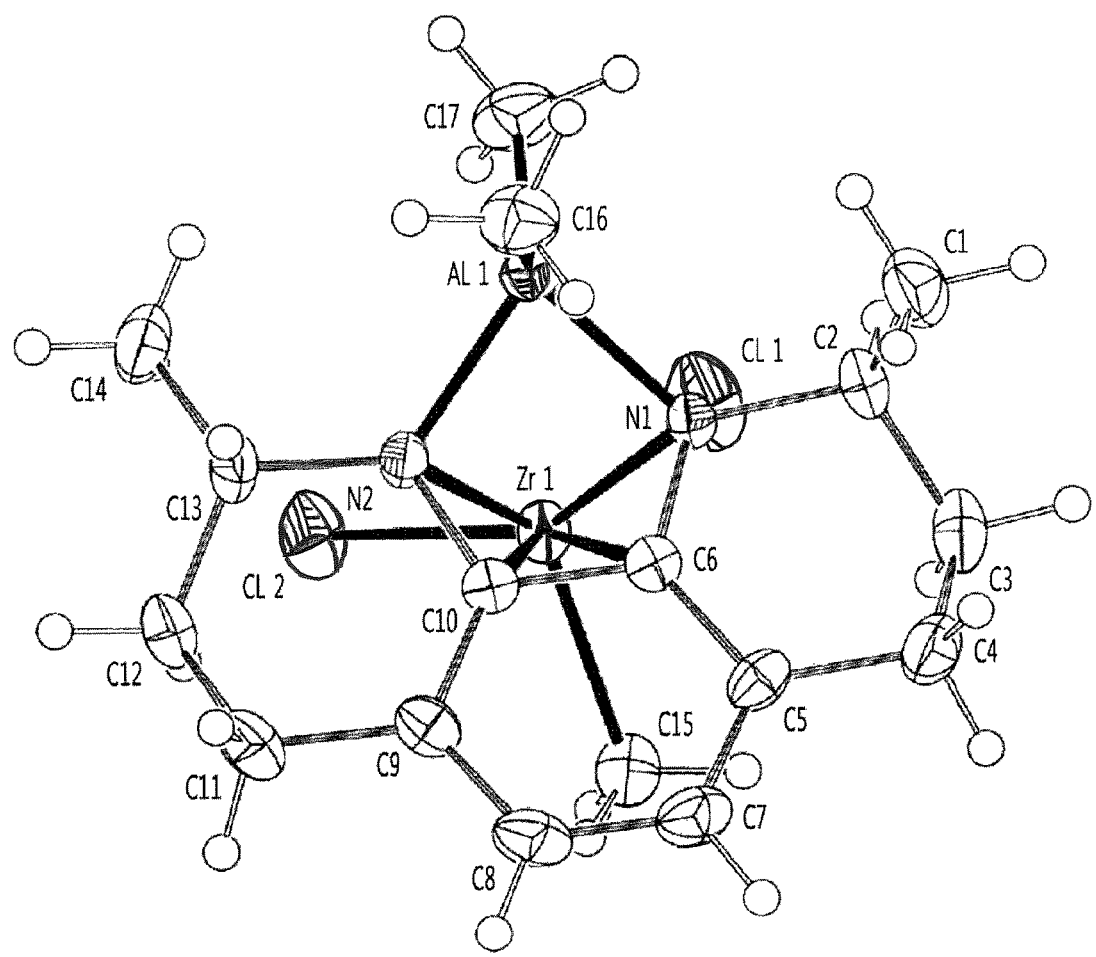

GROUP 4 TRANSITION METAL COMPOUND AND USE THEREOF

CROSS REFERENCE TO RELATED APPLICATION

This application is the U.S. National Phase of International Application No. PCT/KR2015/014187 filed Dec. 23, 2015, which claims the benefit of Korean Patent Application No. 10-2014-0187188 filed Dec. 23, 2014.

BACKGROUND

Technical Field

The present invention relates to a novel Group 4 transition metal compound, a method for preparing the compound, a catalyst composition comprising the compound, and a method for preparing a polyolefin comprising performing a polymerization reaction of olefin monomers in the presence of the catalyst composition.

Background Art

Polyolefins are used as raw materials for manufacturing various products used in daily life, such as shopping bags, greenhouses, fishing nets, packaging materials for cigarettes, ramen pouches, yogurt bottles, battery cases, automobile bumpers, interior materials, shoe soles, washing machines, etc.

Conventional olefin polymers and copolymers such as ethylene polymers, propylene polymers, and ethylene-alpha-olefin copolymers have been prepared by heterogeneous catalysts composed of titanium compounds and alkylaluminum compounds. Recently, metallocene catalysts, which are homogeneous catalysts having an extremely high catalytic activity, have been developed, and methods for preparing a polyolefin using a metallocene catalyst have been studied.

Although metallocene catalysts were already reported in the 1950s, their activity was too low to continue studies thereon. After Professor Kaminsky of Germany first reported in 1976 that methylaluminoxane could be used as a cocatalyst to exhibit a high activity, research on metallocene catalysts was accelerated. Initial single-active-site homogeneous catalysts were in the form of a metallocene compound of a Group 4 metal coordinated by two cyclopentadienyl ligands activated by methylaluminoxane (MAO). Thereafter, it was expanded to the "half-metallocene" catalyst form represented by Dow's constrained geometry catalyst (CGC), and this form of catalysts exhibited more excellent properties in copolymerization than the initial metallocene catalysts. This has been expanding in the form of "post-metallocene" catalysts that do not contain cyclopentadienyl ligands since the beginning of 2000. Most single-active-site catalysts have a similar structure of "LMX$_2$". In particular, M is a central metal, L is a spectator ligand which is always coordinated to the metal, X is an acting ligand composed of a halogen atom, alkyl group, etc., one of which is desorbed as an anion by a cocatalyst to make the central metal as a cation, and a polymer chain grows from the other X.

In the early 2000s, Dow and Symyx jointly utilized high-throughput-screening (HTS) technology to report a new type of a catalyst (*Journal of the American Chemical Society*, 2003, 125: 4306). The catalyst has the structure of "LMX$_3$" and is distinguished from conventionally-known catalysts having the structure of "LMX$_2$". The catalyst of Dow and Symyx is characterized in that the spectator ligand L is in the form of an ether-amido chelate. Thereafter, catalysts having the structure of "LMX$_3$" in which the spectator ligand L is diversified into imine-amido, imine-enamido, aminotropone-iminate, etc. were additionally developed.

However, among the developed catalysts described above, few are commercially applied, and the discovery of a catalyst which exhibits a high activity even at a high temperature of 100° C. or higher, has thermal stability, and exhibits more improved polymerization performance capable of preparing polyolefins of various grades by changing the structures of its central metal and ligand is still required.

SUMMARY

An object of the present invention is to provide a novel Group 4 transition metal compound.

Another object of the present invention is to provide a method for preparing the Group 4 transition metal compound.

A further object of the present invention is to provide a catalyst composition comprising the Group 4 transition metal compound.

A still further object of the present invention is to provide a method for preparing a polyolefin comprising performing a polymerization reaction of olefin monomers in the presence of the catalyst composition comprising the Group 4 transition metal compound.

BRIEF DESCRIPTION OF THE DRAWINGS

FIG. 1 is a diagram illustrating an X-ray diffraction crystal structure of the compound represented by Formula 1-1 comprising zirconium as a central metal according to an exemplary embodiment of the present invention.

DETAILED DESCRIPTION

In an aspect to achieve the above objects, the present invention provides a Group 4 transition metal compound represented by Formula 1 below:

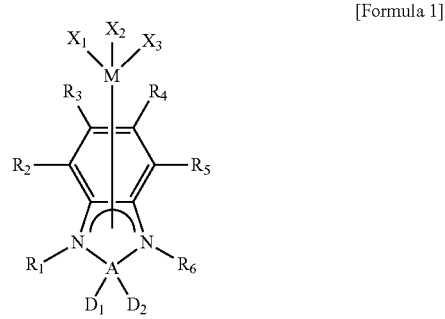

[Formula 1]

wherein, in Formula 1, M is a Group 4 transition metal of Ti, Zr, Hf, or Rf;

each of $X_1$ to $X_3$ is independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene;

each of $R_1$ to $R_6$ is independently hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{6-20}$ aryl, substituted or unsubstituted $C_{7-40}$ alkylaryl, substituted or unsubstituted $C_{7-40}$ arylalkyl, or substituted or unsubstituted $C_{1-20}$ silyl, or $R_1$ and $R_2$, $R_2$ and $R_3$, $R_4$ and $R_5$, or $R_5$ and $R_6$ are linked together to form a substituted or unsubstituted $C_{5-14}$ ring, and A is aluminum or boron;

each of D1 and D2 is independently hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{6-20}$ aryl, substituted or unsubstituted $C_{7-40}$ alkylaryl, substituted or unsubstituted $C_{7-40}$ arylalkyl, or substituted or unsubstituted $C_{1-20}$ silyl; and wherein each substituent is independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene.

As used herein, the term "substitution" may mean that a hydrogen atom is replaced with a functional group such as another atom or atomic group, unless otherwise specified.

In the present invention, alkyl, alkenyl, and alkynyl may be linear, branched, or cyclic.

The present invention provides a Group 4 transition metal compound of a novel structure in which a ligand in the form of a phenanthroline-like chelate is coordinated. As described above, conventional single-active-site homogeneous catalysts have been mainly developed as coordination entities of ligands based on carbon, nitrogen, and oxygen atoms, such as cyclopentadienyl, amido, phenoxo, amine, imine, ether, etc. Recently, a coordination entity of a ligand based on quinoline has been reported, but its structure differs from that of the compound of the present invention, and a bidentate coordination entity based on phenanthroline has not been reported.

Preferably, the above-mentioned novel Group 4 transition metal compound may be a Group 4 transition metal compound represented by Formula 2 below:

[Formula 2]

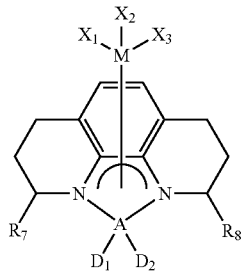

wherein, in Formula 2, M, $X_1$ to $X_3$, A, $D_1$, and $D_2$ are the same as defined above, and each of $R_7$ and $R_8$ is independently hydrogen, or substituted or unsubstituted $C_{1-20}$ alkyl. Each of $X_1$ to $X_3$ may be independently halogen or $C_{1-20}$ alkyl. Preferably, one of $X_1$ to $X_3$ may be methyl and the other two may be chlorine, but they are not limited thereto.

Preferably, each of $R_7$ and $R_8$ may be identical to or different from each other, and may be independently hydrogen, methyl, ethyl, isopropyl, butyl, or phenyl, but is not limited thereto.

In addition, preferably, $D_1$ and $D_2$ may both be methyl, but are not limited thereto.

Non-limiting examples of the compound include Group 4 transition metal compounds represented by formulas selected from the group consisting of

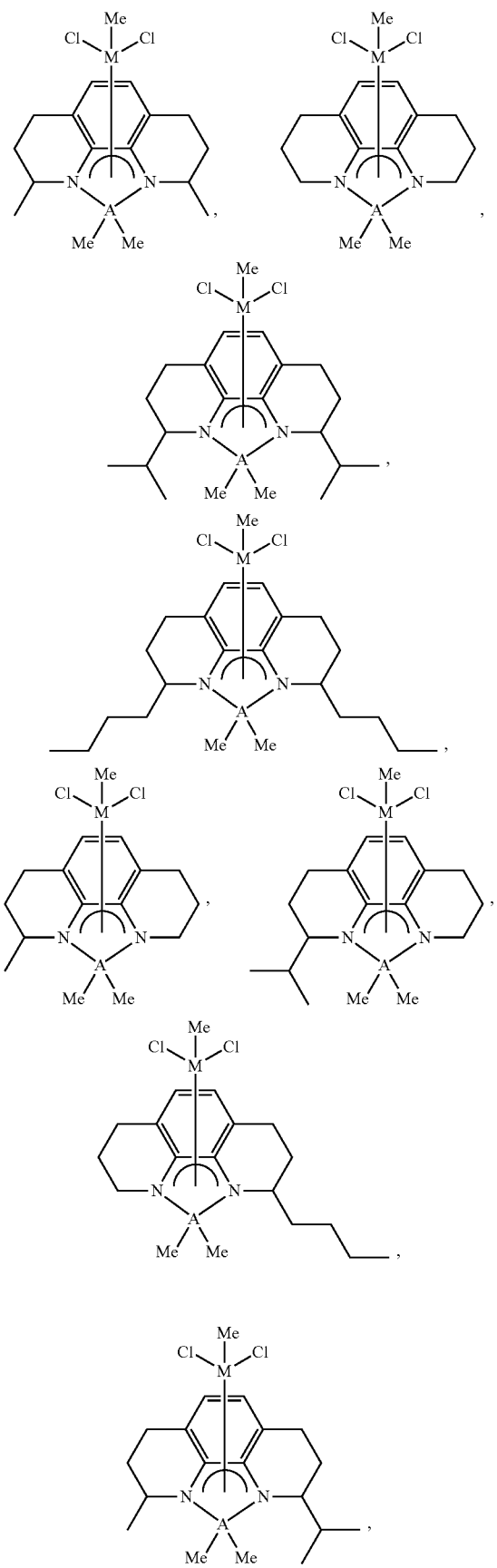

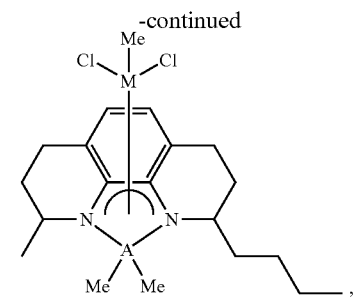

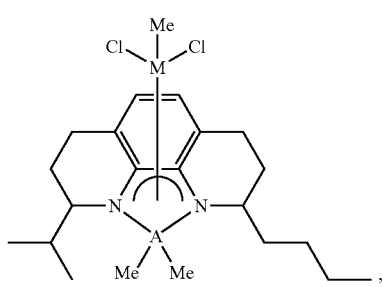

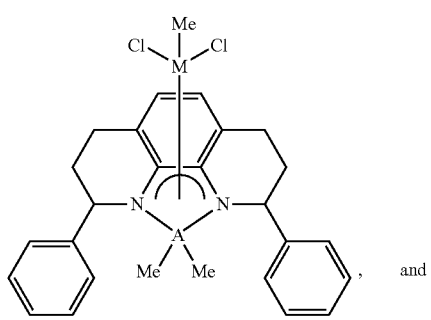

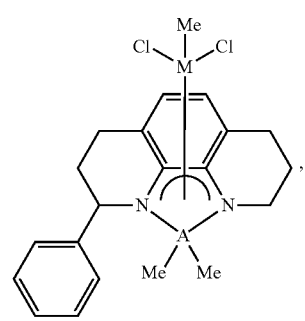

wherein, in the above formulas, M is a Group 4 transition metal of Ti, Zr, Hf, or Rf; A is aluminum or boron; and Me is methyl.

In another aspect, the present invention provides a method for preparing a compound represented by Formula 1 below, comprising reacting a Group 4 transition metal compound represented by Formula 3 below and a compound represented by Formula 4 below:

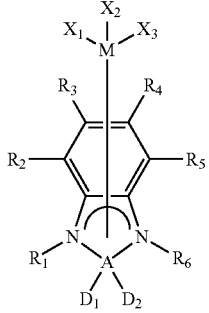

[Formula 1]

[Formula 3]

[Formula 4]

wherein, in the above formulas, M, A, $R_1$ to $R_6$, $X_1$ to $X_3$, $D_1$, and $D_2$ are the same as defined above, and $D_3$ is halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene;

each of $G_1$ and $G_2$ is independently an element of Group 5 or Group 6 of the Periodic Table; and each of $Q_1$ to $Q_6$ is independently hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{6-20}$ aryl, substituted or unsubstituted $C_{7-40}$ alkylaryl, substituted or unsubstituted $C_{7-40}$ arylalkyl, or substituted or unsubstituted $C_{1-20}$ silyl, or any two of $Q_1$ to $Q_3$ or any two of $Q_4$ to $Q_6$ are linked together to form a substituted or unsubstituted $C_{5-14}$ ring comprising or not comprising a heteroelement, wherein each substituent is independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene.

Preferably, the compound may be a Group 4 transition metal compound represented by Formula 5 below:

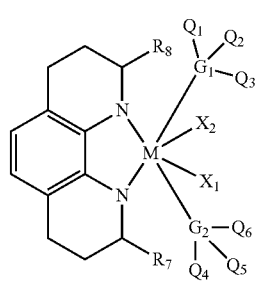

[Formula 5]

wherein, in Formula 5, M, $X_1$ and $X_2$, $C_1$, $C_2$, and $F_1$ to $F_6$ are the same as defined above, and each of $R_7$ and $R_8$ is independently hydrogen, or substituted or unsubstituted $C_{1-20}$ alkyl.

In the reaction, preferably, the compound represented by Formula 3 and the compound represented by Formula 4 may be reacted at an equivalent ratio of 1:3 to 1:7, but are not limited thereto.

In addition, preferably, the reaction can be performed in a hydrocarbon solvent selected from the group consisting of $C_{5-10}$ aliphatic or aromatic hydrocarbon, $C_{1-10}$ saturated or unsaturated hydrocarbon unsubstituted or substituted with halogen atoms, and a mixture thereof. More preferably, the hydrocarbon solvent may be toluene, pentane, hexane, heptane, cyclohexane, methylcyclohexane, benzene, xylene, dichloromethane, chloroethane, dichloroethane, chlorobenzene, or a mixture thereof, but is not limited thereto.

In particular, the hydrocarbon solvent may be used in an amount of 100 parts by weight to 1000 parts by weight based on 100 parts by weight of the sum of the compound represented by Formula 3 and the compound represented by Formula 4, but is not limited thereto.

Preferably, the reaction may be performed at 0° C. to 100° C., and may be performed for 30 minutes to 30 hours, but is not limited thereto.

In a specific exemplary embodiment of the present invention, substituted or unsubstituted 1,2,3,4,7,8,9,10-octahydro-1,10-phenanthroline dissolved in toluene as the compound represented by Formula 3, and a Group 4 transition metal organic compound represented by Formula A were reacted in a reactor at a molar ratio of 1:1 to 1.5 with or without a small amount of tetrahydrofuran to obtain a Group 4 transition metal compound to be used:

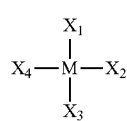

[Formula A]

wherein, in Formula A, M, and $X_1$ to $X_3$ are the same as defined above, and $X_4$ is halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene.

Thereafter, the compound represented by Formula 3, which was obtained using the above method, was reacted with an excess amount, for example, 3 to 7 equivalent amounts, preferably, 5 equivalent amounts of trimethylammonium using toluene as a solvent, to synthesize a Group 4 transition metal compound represented by Formula 1 according to the present invention. For example, the reaction was performed by stirring at 0° C. to 100° C., preferably, at 20° C. to 30° C., for 30 minutes to 30 hours. However, the reaction condition is merely an example, and the preparation method according to the present invention is not limited to the above condition and can be appropriately controlled depending on the combination of the reactants and/or solvent.

Furthermore, after the reaction is completed, the preparation method may additionally be followed by conventional post-treatment processes, for example, removal of a solvent and unreacted compounds, and washing and drying of the product. The removal of the solvent may be performed by evaporation under reduced pressure using a vacuum pump, etc., but the removal method is not limited thereto.

In another aspect, the present invention provides a catalyst composition comprising the Group 4 transition metal compound; and at least one compound selected from the group consisting of a compound represented by Formula 6 below, a compound represented by Formula 7 below, and a compound represented by Formula 8 or Formula 9 below:

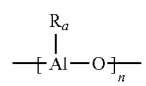

[Formula 6]

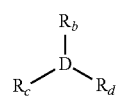

[Formula 7]

$[L-H]^+[Z(A)_4]^-$

[Formula 8]

$[L]^+[Z(A)_4]^-$

[Formula 9]

wherein, in the formulas, $R_a$ is hydrogen, halogen, $C_{1-20}$ alkyl unsubstituted or substituted with halogen, $C_{3-20}$ cycloalkyl unsubstituted or substituted with halogen, $C_{6-40}$ aryl unsubstituted or substituted with halogen, or $C_{6-40}$ alkylaryl unsubstituted or substituted with halogen;

n is an integer of 2 or greater;

D is aluminum or boron;

each of $R_b$ to $R_d$ is identical to or different from each other, and is independently a hydrogen atom, halogen, $C_{1-20}$ alkyl unsubstituted or substituted with halogen, $C_{3-20}$ cycloalkyl unsubstituted or substituted with halogen, $C_{1-20}$ alkoxy, $C_{6-40}$ aryl unsubstituted or substituted with halogen, $C_{6-40}$ alkylaryl, or $C_{6-40}$ arylalkyl unsubstituted or substituted with halogen;

L is a neutral or cationic Lewis acid;

Z is a Group 13 element; and

A is substituted or unsubstituted $C_{6-20}$ aryl or substituted or unsubstituted $C_{1-20}$ alkyl.

Preferably, the catalyst composition of the present invention may comprise the compound represented by Formula 6, the compound represented by Formula 7, or a mixture thereof; and the compound represented by Formula 8 or Formula 9.

Preferably, the catalyst composition of the present invention may comprise the compound represented by Formula 1; the compound represented by Formula 6, the compound represented by Formula 7, or a mixture thereof; and the compound represented by Formula 8 or Formula 9, at a molar ratio of 1:1 to 5:20 to 500.

The compound represented by Formula 6 is aluminoxane, and may preferably be alkylaluminoxane. Non-limiting examples of the aluminoxane may include methylaluminoxane, ethylaluminoxane, isobutylaluminoxane, butylaluminoxane, etc., and preferably, methylaluminoxane can be used, but is not limited thereto. The alkylaluminoxane to be used may be prepared by adding an appropriate amount of water to trialkylaluminum or by reacting a hydrocarbon compound containing water or an inorganic hydrate salt with trialkylaluminum, etc., but is not limited thereto, and commercially available alkylaluminoxanes can be purchased for use. When alkylaluminoxane is prepared by conventional preparation methods, generally, linear and cyclic aluminoxane can be obtained in a mixed form.

The compound represented by Formula 7 above may preferably be an organic compound comprising a Group 13 metal, for example, aluminum or boron. In Formula 7 above, the three substituents are identical to or different from each another. Non-limiting examples of the compound represented by Formula 7 include trimethylaluminum, dimethyl aluminum chloride, methoxydimethylaluminum, methylaluminum dichloride, triethylaluminum, diethylaluminum chloride, methoxydiethylaluminum, ethylaluminum dichloride, tripropylaluminum, dipropylaluminum chloride, propylaluminum dichloride, triisopropyl aluminum, tributylaluminum, triisobutylaluminum, diisobutylaluminum hydride, tricyclopentylaluminum, tripentylaluminum, triisopentylaluminum, trihexyl aluminum, trioctylaluminum, ethyldimethylaluminum, diethyl(methyl)aluminum, triphenylaluminum, tri-p-tolylaluminum, ethoxydimethylaluminum, trimethylboron, triethylboron, triisobutylboron, tripropylboron, tributylboron, tripentafluorophenylboron, etc.

Non-limiting examples of the compound represented by Formula 8 or Formula 9 may include methyldioctadecylammonium tetrakis(pentafluorophenyl)borate ([HNMe$(C_{18}H_{37})_2$]$^+$[B$(C_6F_5)_4$]$^-$), trimethylammonium tetrakis(phenyl)borate, triethylammonium tetrakis(phenyl)borate, tripropylammonium tetrakis(phenyl)borate, tributylammonium tetrakis(phenyl)borate, trimethylammonium tetrakis(p-tolyl)borate, tripropylammonium tetrakis(p-tolyl)borate, trimethylammonium tetrakis(o,p-dimethylphenyl)borate, triethylammonium tetrakis(o,p-dimethylphenyl)borate, trimethylammonium tetrakis(p-trifluoromethylphenyl)borate, tributylammonium tetrakis(p-trifluoromethylphenyl)borate, tributylammonium tetrakis(pentafluorophenyl)borate, diethylammonium tetrakis(pentafluorophenyl)borate, triphenylphosphonium tetrakis(phenyl)borate, trimethylphosphonium tetrakis(phenyl)borate, N,N-diethylanilinium tetrakis(phenyl)borate, N,N-dimethylanilinium tetrakis(pentafluorophenyl)borate, N,N-diethylanilinium tetrakis(pentafluorophenyl)borate, triphenylcarbonium tetrakis(p-trifluoromethylphenyl)borate, triphenylcarbonium tetrakis(pentafluorophenyl)borate, trimethylammonium tetrakis(phenyl)aluminate, triethylammonium tetrakis(phenyl)aluminate, tripropylammonium tetrakis(phenyl)aluminate, tributylammonium tetrakis(phenyl)aluminate, trimethylammonium tetrakis(p-tolyl)aluminate, tripropylammonium tetrakis(p-tolyl)aluminate, triethylammonium tetrakis(o,p-dimethylphenyl)aluminate, tributylammonium tetrakis(p-trifluoromethylphenyl)aluminate, trimethylammonium tetrakis(p-trifluoromethylphenyl)aluminate, tributylammonium tetrakis(pentafluorophenyl)aluminate, N,N-diethylanilinium tetrakis(phenyl)aluminate, N,N-dimethylanilinium tetrakis(phenyl)aluminate, N,N-diethylanilinium tetrakis(pentafluorophenyl)aluminate, diethylammonium tetrakis(pentafluorophenyl)aluminate, triphenylphosphonium tetrakis(phenyl)aluminate, trimethylphosphonium tetrakis(phenyl)aluminate, triethylammonium tetrakis(phenyl)aluminate, tributylammonium tetrakis(phenyl)aluminate, etc., but are not limited thereto. Preferably, methyldioctadecylammonium tetrakis(pentafluorophenyl)borate ([HNMe$(C_{18}H_{37})_2$]$^+$[B$(C_6F_5)_4$]$^-$), N,N-dimethylanilinium tetrakis(pentafluorophenyl)borate, triphenylcarbonium tetrakis(pentafluorophenyl)borate, etc., may be used.

The catalyst composition of the present invention can be prepared by mixing the Group 4 transition metal compound of the present invention and the above-exemplified cocatalyst compound to be in contact with each other. The mixing can be performed under an inert gas atmosphere such as nitrogen or argon without a solvent or in the presence of a hydrocarbon solvent. For example, the mixing can be performed at 0° C. to 100° C., preferably at 10° C. to 30° C. After preparation in a hydrocarbon solvent, etc., the catalyst composition in a uniformly dissolved solution state may be used as is, or it may be used after converting it into a solid powder state by removing the solvent. The catalyst composition in the solid powder state may be obtained by precipitating the catalyst composition in a solution state followed by the solidification of the precipitate. Further, the catalyst composition of the present invention can be used in a form in which a Group 4 transition metal compound and a cocatalyst compound are supported in a carrier such as silica, alumina, or a mixture thereof, or an insoluble particle form of the carrier, but the form of the catalyst composition is not limited thereto.

In a specific exemplary embodiment of the present invention, the cocatalyst compound may comprise a compound represented by Formula 6, a compound represented by Formula 7, a compound represented by Formula 8 or Formula 9, or two or more compounds selected therefrom together. For example, methylaluminoxane, which is a compound represented by Formula 6, and methyldioctadecylammonium tetrakis(pentafluorophenyl)borate ([HNMe$(C_{18}H_{37})_2$]$^+$[B$(C_6F_5)_4$]$^-$), which is a compound represented by Formula 8, were mixed and used. In particular, the catalyst composition can be prepared by sequentially adding and mixing the compound represented by Formula 8 or Formula 9, the compound represented by Formula 6, and/or the compound represented by Formula 7 into a transition metal compound solution which is dissolved in a hydrocarbon solvent. In order to provide a catalyst composition exhibiting a high activity in polyolefin synthesis, the transition metal compound used, the compound represented by Formula 6, and/or the compound represented by Formula 7, and the compound represented by Formula 8 or 9 may be used at the above-mentioned ratio, that is, at a molar ratio of 1:1 to 5:20 to 500. More preferably, they may be used at a molar ratio of 1:1 to 2:100 to 200, but the molar ratio is not limited thereto.

In another aspect, the present invention provides a method for preparing a polyolefin, comprising performing a polymerization reaction of olefin monomers, in the presence of the catalyst composition.

The preparation method of a polyolefin according to the present invention can be achieved by contacting the catalyst composition with two or more molecules of olefin monomers.

In addition, as described above, since the catalyst composition of the present invention can exist not only in a uniform solution state but also in a form supported by a carrier or in the form of an insoluble particle of a carrier, the preparation of a polyolefin according to the present invention can be achieved by liquid-phase, slurry-phase, bulk-phase, or gas-phase polymerization. Further, the conditions for each polymerization reaction may be variously modified depending on the state of the catalyst composition used (homogeneous or heterogeneous such as the supported form), polymerization method (solution polymerization, slurry polymerization, or gas-phase polymerization), and/or desired polymerization results or forms of polymers. The degree of the modification can be easily determined by those skilled in the art. For example, when the polymerization is performed in a liquid phase or slurry phase, a separate solvent may be used or the olefin itself may be used as a medium. For the solvent, propane, butane, pentane, hexane, octane, decane, dodecane, cyclopentane, methylcyclopentane, cyclohexane, methylcyclohexane, benzene, toluene, xylene, dichloromethane, chloroethane, dichloroethane, chlorobenzene, etc., may be used alone, or two or more types thereof may be mixed at a certain ratio and used.

Examples of olefin monomers that can be used in the preparation method according to the present invention include ethylene, alpha-olefins, cycloolefins, etc., and diene olefins, triene olefins, and styrene olefins can also be used. The alpha-olefins include $C_{3-12}$, for example, $C_{3-8}$ aliphatic olefins, and specifically include propylene, 1-butene, 1-hexene, 1-heptene, 1-octene, 1-decene, 1-dodecene, 1-tetradecene, 1-hexadecene, 1-octadecene, 1-eicosene, 4-methyl-1-pentene, 3-methyl-1-pentene, 3-methyl-1-butene, 4,4-dimethyl-1-pentene, 4,4-diethyl-1-hexene, 3,4-dimethyl-1-hexene, etc. The cycloolefins include $C_{3-24}$, for example, $C_{4-18}$ cyclic olefins, and specifically include vinylcyclohexane, vinylcycloheptane, cyclopentene, cycloheptene, cyclobutene, cyclohexene, 3-methylcyclohexene, cyclooctene, tetracyclodecene, octacyclodecene, dicyclopentadiene, norbornene, 5-methyl-2-norbornene, 5-ethyl-2-norbornene, 5-isobutyl-2-norbornene, 5,6-dimethyl-2-norbornene, 5,5,6-trimethyl-2-norbornene, ethylene-norbornene-tetracyclododecene, etc. The diene olefins and triene olefins include $C_{4-26}$ polyenes containing two or three double bonds, and specifically include isoprene, 1,3-butadiene, 1,4-pentadiene, 1,4-hexadiene, 1,5-hexadiene, 1,9-decadiene, 2-methyl-1,3-butadiene, cyclopentadiene, etc. The styrene olefins include styrene or $C_{1-10}$ alkyl, alkoxy or halogenated alkyl, and styrene substituted with halogen, amine, silyl, etc., and specifically styrene, p-methylstyrene, allylbenzene, divinylbenzene, etc.

In the copolymerization of ethylene or propylene as olefin monomers with other alpha-olefins, the amount of alpha-olefins besides ethylene or propylene may be 90 mol % or less of the total monomers. Conventionally, in the case of copolymers with ethylene, the amount of alpha-olefins may be 40 mol % or less, for example, 30 mol % or less, and preferably 20 mol % or less, and in the case of copolymers with propylene, 1 mol % to 90 mol %, preferably 5 mol % to 90 mol %, and more preferably 10 mol % to 70 mol %, but is not limited thereto. Further, alpha-olefins may be copolymerized with cycloolefins, and in particular, the amount of cycloolefins may be in a range of 1 mol % to 50 mol %, for example, 2 mol % to 50 mol %, based on the total amount of the copolymer.

In the method for preparing a polyolefin according to the present invention, the olefin monomer may be used alone or in a combination of two or more types. Preferably, at least one compound selected from the group consisting of ethylene, propylene, 1-butene, 1-hexene, 1-octene, and 1-decene can be used, but the present invention is not limited thereto.

In addition, the olefin monomer may be homopolymerized, or two or more types of olefin monomers or polymers thereof may be alternated, or random- or block-copolymerized.

In the method for preparing a polyolefin according to the present invention, the amount of the catalyst composition is not particularly limited. For example, in the polymerized reaction system, the central metal concentration of the Group 4 transition metal compound of the present invention may be adjusted to be in a range of $1 \times 10^{-5}$ mol/L to $9 \times 10^{-5}$ mol/L and be used. Further, during a polymerization reaction, the temperature and pressure are variable depending on the types of reactants and reaction conditions, etc. and thus are not particularly limited, and it may be performed at a temperature of 0° C. to 200° C. For example, it may be performed at a temperature of 100° C. to 180° C., and in the case of slurry or gas-phase polymerization, it may be performed at a temperature of 0° C. to 120° C., and more preferably, at 60° C. to 100° C. Meanwhile, polymerization pressure may be in a range of 1 bar to 150 bar, for example, 30 bar to 90 bar, and the pressure for polymerization may be controlled to the above range by the injection of an olefin monomer gas used in the reaction.

For example, the polymerization reaction can be performed batchwise, semi-continuously, or continuously. The polymerization reaction can also be performed through two or more steps having different reaction conditions, and the molecular weight of the finally obtained polymer can be adjusted by methods such as changing the polymerization temperature or injecting hydrogen into the reactor, etc.

Since the Group 4 transition metal compound of the present invention exhibits an excellent catalytic activity in polyolefin synthesis reactions, as well as having excellent thermal stability, it can be used for polyolefin synthesis reactions at high temperatures, and by changing the type of a central metal and ligand, the weight average molecular weight of synthesized polyolefins and the octene content in the polymer can be controlled. Therefore, it can be effectively used in polyolefin synthesis processes in which grades are controlled.

EXAMPLES

Hereinafter, the present invention will be described in more detail with reference to the following exemplary embodiments. However, these exemplary embodiments are for explaining the present invention in more detail, and the scope of the invention is not intended to be limited by these exemplary embodiments.

Preparation Example 1: Synthesis of Compound Represented by Formula 2-1 Comprising Zirconium as Central Metal

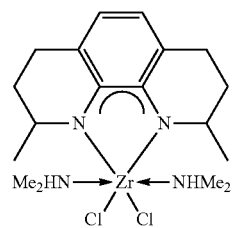

[Formula 2-1]

2,9-Dimethyl-1,2,3,4,7,8,9,10-octahydro-1,10-phenanthroline (0.046 g, 0.21 mmol) and $Zr(NMe_2)_2Cl_2(dme)$ (0.073 mg, 0.21 mmol), which were each dissolved in 0.5 mL of toluene, were mixed. After stirring for 30 minutes, the solvent was removed using a vacuum pump, and the title compound was obtained.

$^1$H NMR (C$_6$D$_6$): δ=6.49 (s, 2H, 5-phenanthroline, 6-phenanthroline), 5.02-4.94 (m, 2H, NCH), 3.00-2.85 (m, 2H, NH), 2.80-2.68 (m, 2H, 4-phenanthroline, 7-phenanthroline), 2.52-2.39 (m, 2H, 4-phenanthroline, 7-phenanthroline), 2.32 (dd, J=2.0, 6.4 Hz, 12H, NH(CH$_3$)$_2$), 1.58-1.50 (m, 4H, 3-phenanthroline, 8-phenanthroline), 1.24 (d, J=6.4 Hz, 6H, CH$_3$);

$^{13}$C{$^1$H} NMR (C$_6$D$_6$): δ=141.60, 119.94, 116.95, 54.30, 41.80, 41.36, 28.97, 22.58, 22.11 ppm.

Preparation Example 2: Synthesis of Compound Represented by Formula 2-2 Comprising Zirconium as Central Metal

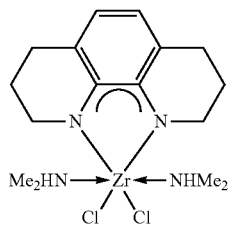

[Formula 2-2]

The title compound was obtained by the same conditions and methods as in Preparation Example 1, except that 1,2,3,4,7,8,9,10-octahydro-1,10-phenanthroline (0.043 g, 0.23 mmol) was used instead of 2,9-dimethyl-1,2,3,4,7,8,9,10-octahydro-1,10-phenanthroline.

$^1$H NMR (C$_6$D$_6$): δ=6.42 (s, 2H, 5-phenanthroline, 6-phenanthroline), 4.34-4.24 (m, 4H, 2-phenanthroline, 9-phenanthroline), 2.72-2.61 (m, 2H, NH), 2.56 (t, J=6.4 Hz, 4H, 4-phenanthroline, 7-phenanthroline), 2.29 (d, J=6.4 Hz, 12H, NH(CH$_3$)$_2$), 1.68-1.58 (m, 4H, 3-phenanthroline, 8-phenanthroline);

$^{13}$C{$^1$H} NMR (C$_6$D$_6$): δ=142.19, 120.36, 118.10, 52.74, 41.13, 28.02, 24.62 ppm.

Preparation Example 3: Synthesis of Compound Represented by Formula 2-3 Comprising Zirconium as Central Metal

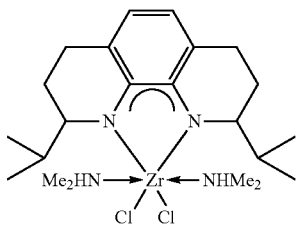

[Formula 2-3]

The title compound was obtained by the same conditions and methods as in Preparation Example 1, except that 2,9-diisopropyl-1,2,3,4,7,8,9,10-octahydro-1,10-phenanthroline (0.068 g, 0.25 mmol) was used instead of 2,9-dimethyl-1,2,3,4,7,8,9,10-octahydro-1,10-phenanthroline.

$^1$H NMR (C$_6$D$_6$): δ=6.44 (s, 2H, 5-phenanthroline, 6-phenanthroline), 4.72-4.60 (m, 2H, NCH), 3.18-3.00 (m, 2H, NH), 2.78-2.62 (m, 2H, 4-phenanthroline, 7-phenanthroline), 2.53-2.41 (m, 4H, 3-phenanthroline, 4-phenanthroline, 7-phenanthroline, 8-phenanthroline), 2.44 (d, J=7.2 Hz, 6H, NH(CH$_3$)$_2$), 2.42 (d, J=6.0 Hz, 6H, NH(CH$_3$)$_2$), 2.10-1.93 (m, 2H, 3-phenanthroline, 8-phenanthroline), 1.58-1.45 (m, 2H, CH), 1.13 (d, J=6.2 Hz, 6H, CH$_3$), 0.91 (d, J=7.2 Hz, 6H, CH$_3$);

$^{13}$C{$^1$H} NMR (C$_6$D$_6$): δ=142.39, 120.04, 117.18, 62.94, 41.97, 35.79, 24.65, 23.60, 20.87, 19.22 ppm.

Preparation Example 4: Synthesis of Compound Represented by Formula 2-4 Comprising Zirconium as Central Metal

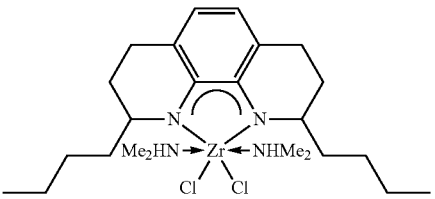

[Formula 2-4]

The title compound was obtained by the same conditions and methods as in Preparation Example 1, except that 2,9-di-n-butyl-1,2,3,4,7,8,9,10-octahydro-1,10-phenanthroline (0.053 g, 0.18 mmol) was used instead of 2,9-dimethyl-1,2,3,4,7,8,9,10-octahydro-1,10-phenanthroline. The reaction was carried out for 12 hours.

$^1$H NMR (C$_6$D$_6$): δ=6.51 (s, 2H, 5-phenanthroline, 6-phenanthroline), 4.88-4.75 (m, 2H, NCH), 3.05-2.89 (m, 2H, NH), 2.75-2.62 (m, 2H, 4-phenanthroline, 7-phenanthroline), 2.52-2.42 (m, 2H, 4-phenanthroline, 7-phenanthroline), 2.36 (dd, J=6.2, 15 Hz, 12H, NH(CH$_3$)$_2$), 1.92-1.80 (m, 4H, 3-phenanthroline, 8-phenanthroline), 1.62-1.28 (m, 12H, CH$_2$), 1.00 (t, J=7.0 Hz, 6H, CH$_3$);

$^{13}$C{$^1$H} NMR (C$_6$D$_6$): δ=141.92, 119.81, 117.03, 58.81, 41.93, 41.40, 35.01, 28.92, 24.47, 23.60, 22.44, 14.85 ppm.

Preparation Example 5: Synthesis of Compound Represented by Formula 2-8 Comprising Zirconium as Central Metal

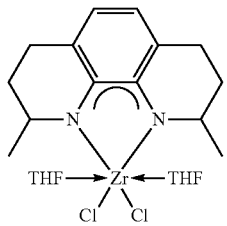

[Formula 2-8]

2,9-Dimethyl-1,2,3,4,7,8,9,10-octahydro-1,10-phenanthroline (0.044 g, 0.21 mmol) and Zr(CH$_2$Ph)$_2$Cl$_2$(Et$_2$O)$_{0.2}$ (0.074 mg, 0.21 mmol) were dissolved in 1.0 mL of toluene, and a small amount of THF was added to dissolve. After stirring for 1 hour, the solvent was removed using a vacuum pump, and the title compound was obtained.

$^1$H NMR (C$_6$D$_6$): δ=1.65 (s, 2H, 5-phenanthroline, 6-phenanthroline), 5.50-5.40 (m, 2H, NCH), 4.32-4.16 (br, 8H, THF), 3.02-2.88 (m, 2H, 4-phenanthroline, 7-phenanthroline), 2.72-2.60 (m, 2H, 4-phenanthroline, 7-phenanthroline), 1.82-1.70 (m, 4H, 3-phenanthroline, 8-phenanthroline), 1.42 (d, J=6.8 Hz, 6H, CH$_3$), 1.34-1.20 (br, 8H, THF);
$^{13}$C{$^1$H} NMR (C$_6$D$_6$): δ=141.32, 119.52, 116.81, 76.31, 54.10, 29.23, 25.55, 22.66, 22.23 ppm.

Preparation Example 6: Synthesis of Compound Represented by Formula 2-9 Comprising Zirconium as Central Metal

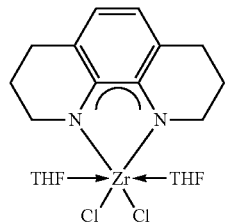

[Formula 2-9]

The title compound was obtained by the same conditions and methods as in Preparation Example 5, except that 1,2,3,4,7,8,9,10-octahydro-1,10-phenanthroline (0.042 g, 0.22 mmol) was used instead of 2,9-dimethyl-1,2,3,4,7,8,9,10-octahydro-1,10-phenanthroline.
$^1$H NMR (C$_6$D$_6$): δ=6.49 (s, 2H, 5-phenanthroline, 6-phenanthroline), 4.68-4.50 (m, 4H, NCH), 4.17 (br, 8H, THF), 2.75-2.60 (m, 4H, 4-phenanthroline, 7-phenanthroline), 1.80-1.70 (m, 4H, 3-phenanthroline, 8-phenanthroline), 1.18 (br, 8H, THF);
$^{13}$C{$^1$H} NMR (C$_6$D$_6$): δ=142.60, 119.76, 117.95, 75.91, 52.74, 28.15, 25.69, 25.19 ppm.

Preparation Example 7: Synthesis of Compound Represented by Formula 2-10 Comprising Zirconium as Central Metal

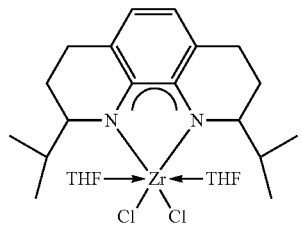

[Formula 2-10]

2,9-Diisopropyl-1,2,3,4,7,8,9,10-octahydro-1,10-phenanthroline (0.047 g, 0.17 mmol) and Zr(CH$_2$Ph)$_2$Cl$_2$(Et$_2$O)$_{0.2}$ (0.080 mg, 0.22 mmol) were dissolved in 1.0 mL of toluene, and a small amount of THF was added to dissolve. Since Zr(CH$_2$Ph)$_2$Cl$_2$(Et$_2$O)$_{0.2}$ is unstable at room temperature, an excess amount of 1.3 equivalents thereof was used. After stirring for 1 hour, the solvent was removed using a vacuum pump, and after dissolving in toluene again, the excess Zr(CH$_2$Ph)$_2$Cl$_2$(Et$_2$O)$_{0.2}$ was filtered. Thereafter, the solvent was removed using a vacuum pump, and the title compound was obtained.
$^1$H NMR (C$_6$D$_6$): δ=6.56 (s, 2H, 5-phenanthroline, 6-phenanthroline), 5.22-5.10 (m, 2H, NCH), 4.31-4.12 (br, 8H, THF), 2.87-2.74 (m, 2H, 4-phenanthroline, 7-phenanthroline), 2.61-2.50 (m, 2H, 4-phenanthroline, 7-phenanthroline), 2.01-1.91 (m, 2H, 3-phenanthroline, 8-phenanthroline), 1.91-1.80 (m, 2H, 3-phenanthroline, 8-phenanthroline), 1.69-1.54 (m, 4H, CH$_2$), 1.54-1.34 (m, 8H, CH$_2$), 1.34-1.18 (br, 8H, THF), 0.99 (t, J=7.0 Hz, 6H, CH$_3$);
$^{13}$C{$^1$H} NMR (C$_6$D$_6$): δ=141.54, 119.48, 116.94, 76.36, 58.66, 35.21, 28.88, 25.65, 25.13, 23.84, 22.51, 14.79 ppm.

Preparation Example 8: Synthesis of Compound Represented by Formula 2-11 Comprising Zirconium as Central Metal

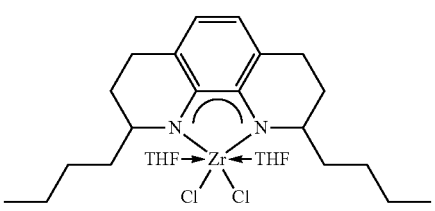

[Formula 2-11]

The title compound was obtained by the same conditions and methods as in Preparation Example 7, except that 2,9-di-n-butyl-1,2,3,4,7,8,9,10-octahydro-1,10-phenanthroline (0.050 g, 0.17 mmol) was used instead of 2,9-diisopropyl-1,2,3,4,7,8,9,10-octahydro-1,10-phenanthroline.
$^1$H NMR (C$_6$D$_6$): δ=6.52 (s, 2H, 5-phenanthroline, 6-phenanthroline), 4.92-2.82 (m, 2H, NCH), 4.39-4.08 (br, 8H, THF), 2.89 (m, 2H, 4-phenanthroline, 7-phenanthroline), 2.60-2.50 (m, 2H, 4-phenanthroline, 7-phenanthroline), 2.40-2.28 (m, 2H, 3-phenanthroline, 8-phenanthroline), 2.12-2.02 (m, 2H, 3-phenanthroline, 8-phenanthroline), 1.67-1.55 (m, 2H, CH), 1.33-1.18 (br, 8H, THF), 1.22 (d, J=6.8 Hz, 6H, CH$_3$), 1.02 (d, J=6.8 Hz, 6H, CH$_3$);
$^{13}$C{$^1$H} NMR (C$_6$D$_6$): δ=141.96, 119.63, 116.98, 76.49, 63.29, 34.54, 25.62, 24.45, 24.15, 21.42, 19.94 ppm.

Preparation Example 9: Synthesis of Compound Represented by Formula 1-1 Comprising Zirconium as Central Metal

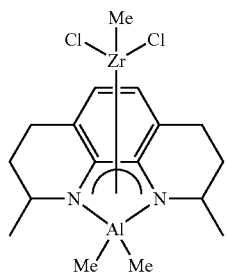

[Formula 1-1]

The compound represented by Formula 2-1 comprising zirconium as a central metal, which was prepared according to Preparation Example 1, and trimethylaluminum (5 equivalent amounts) were reacted in toluene at room temperature for 30 minutes. The solvent was removed using a vacuum pump, and the title compound was obtained by recrystallization at −35° C.

$^1$H NMR (C$_6$D$_6$): δ=6.56 (dd, J=7.6, 15.6 Hz, 2H, 5-phenanthroline, 6-phenanthroline), 3.72-3.60 (m, 1H, NCH), 3.15-3.03 (m, 1H, NCH), 2.38-2.13 (m, 3H, 4-phenanthroline, 7-phenanthroline), 2.13-2.00 (m, 1H, 4-phenanthroline, 7-phenanthroline), 1.76-1.62 (m, 1H, 3-phenanthroline, 8-phenanthroline), 1.50-1.40 (m, 1H, 3-phenanthroline, 8-phenanthroline), 1.43 (d, J=6.8 Hz, 3H, CH3), 1.32-1.22 (m, 1H, 3-phenanthroline, 8-phenanthroline), 1.15-1.02 (m, 1H, 3-phenanthroline, 8-phenanthroline), 1.06 (d, J=6.4 Hz, 3H, CH3), 0.46 (s, 3H, ZrCH$_3$), −0.09 (s, 3H, AlCH$_3$), −0.73 (s, 3H, AlCH$_3$) ppm.

Preparation Example 10: Synthesis of Compound Represented by Formula 1-2 Comprising Zirconium as Central Metal

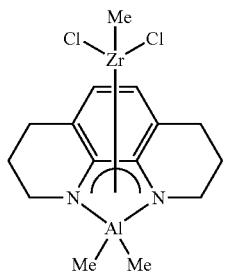

[Formula 1-2]

The title compound was obtained by the same conditions and methods as in Preparation Example 9, except that the compound represented by Formula 2-2 comprising zirconium as a central metal prepared according to Preparation Example 2 was used instead of the compound represented by Formula 2-1 comprising zirconium as a central metal.

$^1$H NMR (C$_6$D$_6$): δ=6.50 (s, 2H, 5-phenanthroline, 6-phenanthroline), 3.63-3.46 (m, 2H, NCH), 2.86-2.68 (m, 2H, NCH), 2.22-1.94 (m, 4H, 4-phenanthroline, 7-phenanthroline), 1.64-1.44 (m, 2H, 3-phenanthroline, 8-phenanthroline), 1.44-1.22 (m, 2H, 3-phenanthroline, 8-phenanthroline), 0.51 (s, 3H, ZrCH$_3$), −0.13 (s, 3H, AlCH$_3$), −0.77 (s, 3H, AlCH$_3$) ppm.

Examples 1 to 10: Synthesis of Ethylene and 1-Octene Copolymer

A solution (1.0 M, 1-octene 4.0 g, 30 mL), in which 1-octene was dissolved in methylcyclohexane as a comonomer, and a methylaluminoxane solution (scavenger, 7% Al toluene solution, 29 mg, 75 mmol Al) as a cocatalyst to remove water and oxygen were added to a high-pressure polymerization reactor in a dry box, and the temperature of the high-pressure polymerization reactor was elevated to 100erization reactor in a dry box, and the temperature of the hmmol) prepared in each of Preparation Examples 1 to 10 was dissolved in toluene, and methyldioctadecylammonium tetrakis(pentafluorophenyl)borate ([HNMe(C$_{18}$H$_{37}$)$_2$]$^+$[B(C$_6$F$_5$)$_4$]$^−$, 1.2 mmol) and a methylaluminoxane solution (7% Al toluene solution, 19 mg, 50 mmol Al, Al/Hf or Zr=125) were added in sequence. Toluene was further added to the reaction mixture to make a final solution volume of 3 mL to prepare an activated catalyst composition. After injecting the catalyst composition into the high-pressure polymerization reactor using a syringe, ethylene was injected at a pressure of 435 psig in the temperature range shown in Table 1 below, and ethylene and 1-octene were polymerized for 3 minutes. Ethylene gas was vented, and 10 mL of methanol was added at 0° C. to finish the reaction. After filtering the white solid compound formed, it was dried in a vacuum oven at 150 polymerization reactor usrepare a polyolefin, that is, an ethylene and 1-octene copolymer. The results of each experiment are shown in Table 1.

TABLE 1

| Example | Catalyst | Temperature (° C.) | Yield (g) | Activity | [1-octene] (mol) | M$_w$ × 10$^{-3}$ | M$_w$/M$_n$ | T$_m$ (° C.) |
|---|---|---|---|---|---|---|---|---|
| 1 | Preparation Example 1 | 100-112 | 1.70 | 34 | 2.89 | 16,360 | 3.39 | 115 |
| 2 | Preparation Example 2 | 100-112 | 1.52 | 30 | 3.41 | 69,587 | 17.30 | 109/121 |
| 3 | Preparation Example 3 | 100-111 | 0.97 | 19 | — | 333,100 | 30.47 | 135 |
| 4 | Preparation Example 4 | 100-105 | 0.84 | 8 | — | 109,096 | 19.72 | 124/108 |
| 5 | Preparation Example 5 | 100-131-129 | 3.65 | 73 | 3.05 | 10,408 | 1.99 | 116 |
| 6 | Preparation Example 6 | 100-120 | 2.77 | 55 | 3.07 | 55,926 | 11.56 | 123/108 |
| 7 | Preparation Example 7 | 100-113 | 0.71 | 14 | 3.53 | 375,864 | 21.45 | 133 |
| 8 | Preparation Example 8 | 100-105-102 | 0.58 | 12 | — | 19,932 | 5.84 | 113/124 |
| 9 | Preparation Example 9 | 100-127-124 | 3.71 | 74 | 3.16 | 11,590 | 2.19 | 114 |
| 10 | Preparation Example 10 | 100-119-112 | 2.35 | 47 | 3.46 | 69,108 | 14.28 | 124/110 |

Property Evaluation (1) Activity unit: kg (polyolefin)/mmol (catalyst central metal). hr (2) 1-Octene content (unit: mol %): 1-Octene content in the polyolefin obtained through $^1$H NMR spectral analysis.

(3) Weight average molecular weight (Mw, unit: g/mol): Measured using gel permeation chromatography (GPC) based on polystyrene.

(4) Melting temperature (T$_m$, unit: ting temperature (Tation chromatography (GPC) based on polystyreneenermeation chromatography (GPC) based on polystyreneolymer. The results of each experiment are shown in Table 1. ylenethereat for 5 minutes, then the temperature was lowered to 30 b, and the temperature was raised again to set the maximum peak of a DSC curve as the melting temperature. In particular, the rate of increasing and decreasing the temperature was 10 erature was raised again to set the maximum peak of a DSC curve as the melature was rising.

As shown in Table 1 above, when a polyolefin was prepared using the catalyst composition comprising the Group 4 transition metal compound according to the present invention, it was confirmed that the resulting polyolefin exhibited a high activity even at a high temperature of 100 activity even at a high omprising the Group 4 transition metal compound accordings prepared according to Preparation Examples 5 and 9 exhibited an excellent catalytic activity (Examples 5 and 9). Meanwhile, the polyolefin synthesized using the transition metal compound prepared according to Preparation Example 7 as a catalyst showed a relatively high weight average molecular weight and also showed a high 1-octene content. It was confirmed that the molecular weight of the polyolefin produced from the above results can be adjusted (in the range of weight average molecular weight of 10,000 to 400,000) depending on the structure of the coordinated ligand and the type of the central metal of the transition metal compound contained in the catalyst composition used, and it was confirmed that the 1-octene content also varied within a certain range (2.89 mol % to 3.53 mol %).

Simple modifications and variations of the present invention can easily be made by those skilled in the art, and it is understood that such modifications and variations are included within the scope of the present invention.

The invention claimed is:

1. A Group 4 transition metal compound represented by Formula 1 below:

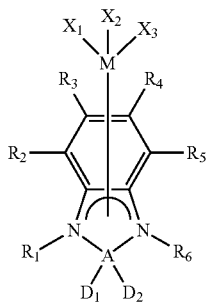

[Formula 1]

wherein M is a Group 4 transition metal of Ti, Zr, or Hf;
each of $X_1$ and $X_2$ is independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene, with the proviso that, when one of $X_1$ and $X_2$ is $C_{1-20}$ alkylidene, then the other is absent;
$X_3$ is halogen $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, or $C_{6-20}$ arylamido;
each of $R_1$ to $R_6$ is independently hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{6-20}$ aryl, substituted or unsubstituted $C_{7-40}$ alkylaryl, substituted or unsubstituted $C_{7-40}$ arylalkyl, or substituted or unsubstituted $C_{1-20}$ silyl, or $R_1$ and $R_2$, $R_2$ and $R_3$, $R_4$ and $R_5$, or $R_5$ and $R_6$ are linked together to form a substituted or unsubstituted $C_{5-14}$ ring, and
A is aluminum or boron;
each of D1 and D2 is independently hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{6-20}$ aryl, substituted or unsubstituted $C_{7-40}$ alkylaryl, substituted or unsubstituted $C_{7-40}$ arylalkyl, or substituted or unsubstituted $C_{1-20}$ silyl; and
wherein each substituent is independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene.

2. The Group 4 transition metal compound of claim 1, wherein the compound is represented by Formula 2 below:

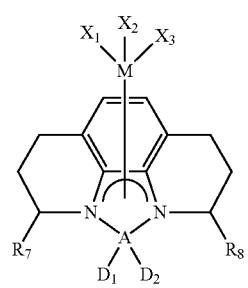

[Formula 2]

wherein each of $R_7$ and $R_8$ is independently hydrogen, or substituted or unsubstituted $C_{1-20}$ alkyl.

3. The Group 4 transition metal compound of claim 2, wherein each of $X_1$ to $X_3$ is independently halogen or $C_{1-20}$ alkyl.

4. The Group 4 transition metal compound of claim 3, wherein one of $X_1$ to $X_3$ is methyl and the other two are chlorine.

5. The Group 4 transition metal compound of claim 2, wherein $R_7$ and $R_8$ are the same or different from each other and each is independently selected from the group consisting of hydrogen, methyl, ethyl, isopropyl, butyl, and phenyl.

6. The Group 4 transition metal compound of claim 2, wherein $D_1$ and $D_2$ are both methyl.

7. The Group 4 transition metal compound of claim 1, wherein the compound is represented by a formula selected from the group consisting of

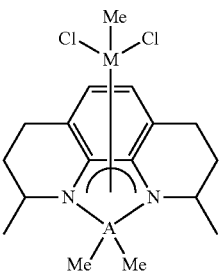 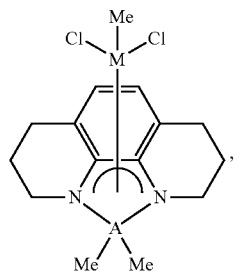

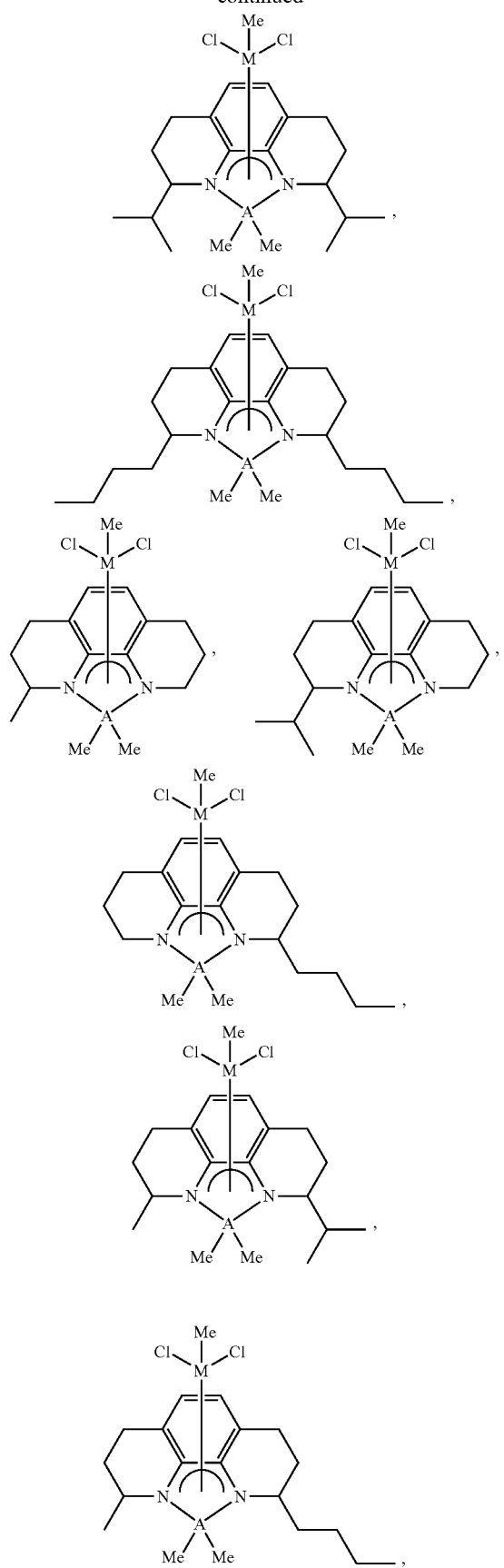
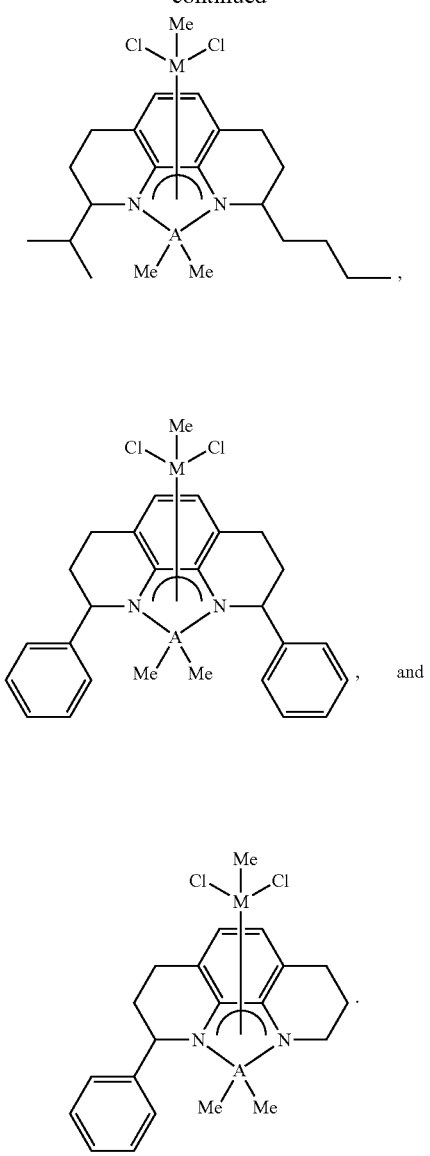
8. A method for preparing a compound represented by Formula 1 below, comprising reacting a Group 4 transition metal compound represented by Formula 3 below and a compound represented by Formula 4 below:
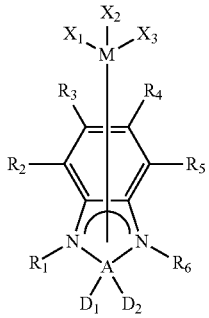
[Formula 1]

[Formula 3]

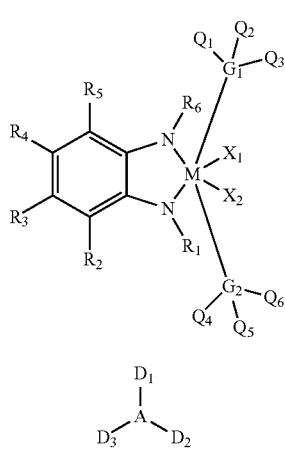

[Formula 4]

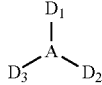

wherein M is a Group 4 transition metal of Ti, Zr, or Hf;
each of $X_1$ and $X_2$ is independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene, with the proviso that, when one of $X_1$ and $X_2$ is $C_{1-20}$ alkylidene, then the other is absent;
$X_3$ is halogen $C_{1-20}$ alkyl, $C_{2-20}$ alkenyl, $C_{2-20}$ alkenyl, $C_{6-20}$ aryl, $C_{7-40}$ alkylaryl, or $C_{7-40}$ arylalkyl;
each of $R_1$ to $R_6$ is independently hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{6-20}$ aryl, substituted or unsubstituted $C_{7-40}$ alkylaryl, substituted or unsubstituted $C_{7-40}$ arylalkyl, or substituted or unsubstituted $C_{1-20}$ silyl, or
$R_1$ and $R_2$, $R_2$ and $R_3$, $R_4$ and $R_5$, or $R_5$ and $R_6$ are linked together to form a substituted or unsubstituted $C_{5-14}$ ring, and
A is aluminum or boron;
each of $D_1$ and $D_2$ is independently hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{6-20}$ aryl, substituted or unsubstituted $C_{7-40}$ alkylaryl, substituted or unsubstituted $C_{7-40}$ arylalkyl, or substituted or unsubstituted $C_{1-20}$ silyl; and
$D_3$ is halogen, $C_{1-20}$ alkyl, $C_{2-20}$ alkenyl, $C_{2-20}$ alkynyl, $C_{6-20}$ aryl, $C_{7-40}$ alkylaryl, or $C_{7-40}$ arylalkyl;
each of $G_1$ and $G_2$ is independently an element of Group 5 or Group 6 of the Periodic Table; and
each of $Q_1$ to $Q_6$ is independently hydrogen, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{6-20}$ aryl, substituted or unsubstituted $C_{7-40}$ alkylaryl, substituted or unsubstituted $C_{7-40}$ arylalkyl, or substituted or unsubstituted $C_{1-20}$ silyl, or
any two of $Q_1$ to $Q_3$ or any two of $Q_4$ to $Q_6$ are linked together to form a substituted or unsubstituted $C_{5-14}$ ring comprising or not comprising a heteroelement,
with the proviso that, when $G_1$ is an element of Group 6 of the Periodic Table, then any one of $Q_1$ to $Q_3$ is absent, and when $G_2$ is an element of Group 6 of the Periodic Table, then any one of $Q_4$ to $Q_6$ is absent,
wherein each substituent is independently halogen, $C_{1-20}$ alkyl, $C_{2-20}$ alkenyl, $C_{2-20}$ alkynyl, $C_{6-20}$ aryl, $C_{7-40}$ alkylaryl, $C_{7-40}$ arylalkyl, $C_{1-20}$ alkylamido, $C_{6-20}$ arylamido, or $C_{1-20}$ alkylidene.

9. The method of claim 8, wherein the Group 4 transition metal compound represented by Formula 3 has the structure of Formula 5:

[Formula 5]

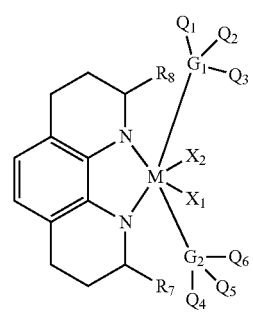

wherein
each of $R_7$ and $R_5$ is independently hydrogen, or substituted or unsubstituted $C_{1-20}$ alkyl.

10. The method of claim 8, wherein the compound represented by Formula 3 and the compound represented by Formula 4 are reacted at an equivalent ratio of 1:3 to 1:7.

11. The method of claim 8, wherein said reacting is performed in a hydrocarbon solvent selected from the group consisting of $C_{5-10}$ aliphatic or aromatic hydrocarbon, $C_{1-10}$ saturated or unsaturated hydrocarbon unsubstituted or substituted with halogen atoms, and a mixture thereof.

12. The method of claim 11, wherein the hydrocarbon solvent is selected from the group consisting of toluene, pentane, hexane, heptane, cyclohexane, methylcyclohexane, benzene, xylene, dichloromethane, chloroethane, dichloroethane, chlorobenzene, and a mixture thereof.

13. The method of claim 12, wherein the hydrocarbon solvent is used in an amount of 100 parts by weight to 1000 parts by weight based on 100 parts by weight of the sum of the compound represented by Formula 3 and the compound represented by Formula 4.

14. The method of claim 8, wherein said reacting is performed at 0° C. to 100° C.

15. The method of claim 8, wherein said reacting is performed for 30 minutes to 30 hours.

16. A catalyst composition, comprising:
the Group 4 transition metal compound according to claim 1; and
at least one compound selected from the group consisting of a compound represented by Formula 6 below, a compound represented by Formula 7 below, and a compound represented by Formula 8 or Formula 9 below:

[Formula 6]

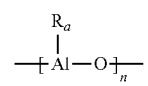

[Formula 7]

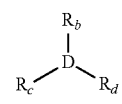

[Formula 8]

-continued $$[L]^+[Z(A)_4]^- \quad \text{[Formula 9]}$$

wherein $R_a$ is hydrogen, halogen, $C_{1-20}$ alkyl unsubstituted or substituted with halogen, $C_{3-20}$ cycloalkyl unsubstituted or substituted with halogen, $C_{6-40}$ aryl unsubstituted or substituted with halogen, or $C_{6-40}$ alkylaryl unsubstituted or substituted with halogen;

n is an integer of 2 or greater;

D is aluminum or boron;

each of $R_b$ to $R_d$ is identical to or different from each other, and is independently a hydrogen atom, halogen, $C_{1-20}$ alkyl unsubstituted or substituted with halogen, $C_{3-20}$ cycloalkyl unsubstituted or substituted with halogen, $C_{1-20}$ alkoxy, $C_{6-40}$ aryl unsubstituted or substituted with halogen, $C_{6-40}$ alkylaryl, or $C_{6-40}$ arylalkyl unsubstituted or substituted with halogen;

$[L]^+$ is a Lewis acid;

L' is a Lewis base;

Z is a Group 13 element; and

A is substituted or unsubstituted $C_{6-20}$ aryl or substituted or unsubstituted $C_{1-20}$ alkyl.

17. The catalyst composition of claim 16, comprising:
the compound represented by Formula 6, the compound represented by Formula 7, or a mixture thereof; and
the compound represented by Formula 8 or Formula 9.

18. The catalyst composition of claim 17, comprising:
the Group 4 transition metal compound represented by Formula 1;
the compound represented by Formula 6, the compound represented by Formula 7, or a mixture thereof; and
the compound represented by Formula 8 or Formula 9, at a molar ratio of 1:1 to 5:20 to 500.

19. A method for preparing a polyolefin, comprising performing a polymerization reaction of olefin monomers, in the presence of the catalyst composition according claim 16.

20. The method of claim 19, wherein the olefin monomers comprise at least one compound selected from the group consisting of ethylene, propylene, 1-butene, 1-hexene, 1-octene, and 1-decene.

* * * * *